US007120493B2

(12) United States Patent
Propp et al.

(10) Patent No.: US 7,120,493 B2
(45) Date of Patent: Oct. 10, 2006

(54) SHOCK LEAD IMPEDANCE MEASUREMENT TO ENSURE SAFE DELIVERY OF SHOCK THERAPY TO MAINTAIN CIRCUIT INTEGRITY

(75) Inventors: Hal M. Propp, Oakdale, MN (US); Gary T. Seim, Minneapolis, MN (US); Michael L. Favet, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 623 days.

(21) Appl. No.: 10/210,790

(22) Filed: Jul. 31, 2002

(65) Prior Publication Data

US 2004/0024424 A1    Feb. 5, 2004

(51) Int. Cl.
*A61N 1/39* (2006.01)
(52) U.S. Cl. .......................................................... 607/8
(58) Field of Classification Search ................ 607/4–8, 607/27, 63
See application file for complete search history.

(56) References Cited

U.S. PATENT DOCUMENTS

| 5,003,975 | A | 4/1991 | Hafelfinger et al. .. 128/419 PG |
| 5,097,830 | A * | 3/1992 | Eikefjord et al. ............... 607/8 |
| 5,201,865 | A | 4/1993 | Kuehn .................. 128/419 PT |
| 5,224,475 | A | 7/1993 | Berg et al. ............... 128/419 D |
| 5,476,485 | A | 12/1995 | Weinberg et al. .............. 607/28 |
| 5,507,786 | A | 4/1996 | Morgan et al. ................ 607/27 |
| 5,534,018 | A | 7/1996 | Wahlstrand et al. ........... 607/27 |
| 5,755,742 | A | 5/1998 | Schuelke et al. .............. 607/27 |
| 5,897,577 | A | 4/1999 | Cinbis et al. .................. 607/28 |
| H1929 | H | 12/2000 | Citak .......................... 607/28 |
| 6,317,628 | B1 | 11/2001 | Linder et al. ................ 600/911 |
| 6,317,633 | B1 | 11/2001 | Jorgenson et al. ............ 607/28 |
| 2001/0031992 | A1 | 10/2001 | Fishler et al. |

FOREIGN PATENT DOCUMENTS

EP    0280526    8/1988

\* cited by examiner

*Primary Examiner*—Scott M. Getzow
(74) *Attorney, Agent, or Firm*—Schwegman, Lundberg, Woessner, & Kluth, P.A.

(57) ABSTRACT

An apparatus and method of automatically measuring the lead impedance of a high energy shock lead before delivery of high energy therapy used to treat heart arrhythmia. In one example, an impedance measurement circuit measures the impedance between electrodes in a plurality of pairs of electrodes. The measured lead electrode impedance is compared to a predetermined value to detect if the lead is shorted to another lead. If a high-energy shock electrode is shorted to another lead, a shorted lead indicator is set to a fault state. Based on the state of the shorted lead indicator, a processor prevents or allows the delivery of high energy therapy. By checking for a lead short before delivery of the therapy, all of the energy of the therapy is delivered to the patient rather than being bypassed by a shorted lead connection.

18 Claims, 5 Drawing Sheets

SHOCK LEAD IMPEDANCE MEASUREMENT TO ENSURE SAFE DELIVERY OF SHOCK THERAPY TO MAINTAIN CIRCUIT INTEGRITY

TECHNICAL FIELD

This document relates to pacemakers, defibrillators, and any other devices that are capable of diagnosing and treating cardiac arrhythmia, and in particular, to an apparatus and method for ensuring effective delivery of shock therapy by automatic measurement of shock lead impedance.

BACKGROUND

Pacemakers deliver timed sequences of low energy electrical stimuli, called pace pulses, to the heart, such as via an intravascular lead (hereinafter referred to as a "lead"). By properly timing the delivery of pace pulses, the heart can be induced to contract in proper rhythm, greatly improving its pumping efficiency.

Defibrillators are devices capable of delivering higher energy electrical stimuli to the heart. A defibrillator is capable of delivering a high energy electrical stimulus that is sometimes referred to as a defibrillation countershock. The countershock interrupts a fibrillation, allowing the heart to reestablish a normal rhythm for efficient pumping of blood.

One problem that may arise is if a shock lead dislodges and the shock electrode shorts to either a pacing lead or another shock lead. The short may cause all of the energy from the countershock to be delivered internal to the device itself instead of to the heart which may damage the device. There is a need in the art for detection of shorted leads.

SUMMARY

This document discusses an apparatus and method of automatically measuring the lead impedance of a high energy shock lead before delivery of high energy therapy used to treat heart arrhythmia. In one example, an impedance measurement circuit measures the impedance between different pairs of electrodes. The measured lead electrode impedance is compared to a predetermined value to detect if the lead is shorted to another lead. If a high-energy shock electrode is shorted to another lead, a shorted lead indicator is set to a fault state. Based on the state of the shorted lead indicator, a processor prevents or allows the delivery of high energy therapy. By checking for a lead short before delivery of the therapy, all of the energy of the therapy is delivered to the patient rather than being bypassed by a shorted lead connection.

In one example, the lead impedance is measured after the defibrillator or defibrillator/pacemaker device has charged in preparation for a countershock. If the shorted lead is not set to a fault state and the lead impedance is greater than a predetermined value, the delivery of shock therapy is continued. If the shorted lead indicator is set to a fault state or the measured lead impedance is less than a predetermined value, shock therapy is aborted.

In another example, the lead impedance is measured while the device is charging in preparation for a countershock. If the charging is complete, the shorted lead indicator is not set to a fault state, and if the lead impedance is greater than a predetermined value, the delivery of shock therapy is continued. The delivery is also continued if the charging completed before the impedance measurement completed and the shorted lead indicator is not set to a fault state. The delivery of the shock therapy is aborted if the charging completed and either the shorted lead indicator was set or the lead impedance is less than or equal to a predetermined value.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part thereof, and in which is shown by way of illustration specific embodiments in which the invention may be practiced. Other embodiments may be used and structural changes may be made without departing from the scope of the present invention.

The various embodiments will generally be discussed in the context of cardiac therapy given by delivering shock therapy to the coronary sinus region, having electrodes coupled to the coronary sinus region and the right atrial and ventricular regions. However, the methods described herein can be adapted to treat other forms cardiac arrhythmia by disposing leads in other selected cardiac regions. Furthermore, the methods described herein can also be adapted to unichamber therapies, having multiple lead sites within a single chamber.

Figure 1:
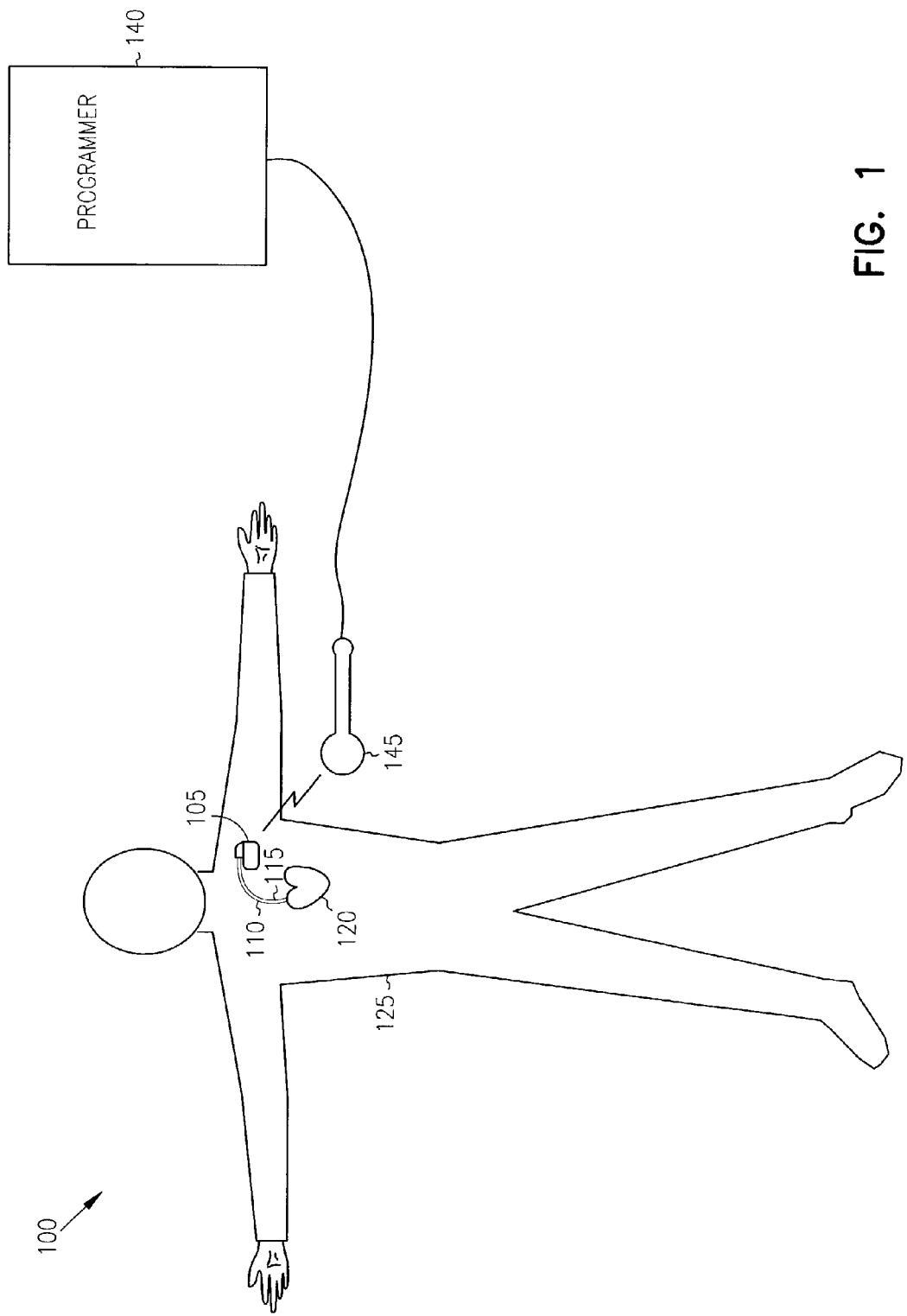
FIG. 1 is a general illustration of one embodiment of portions of a system to treat cardiac arrhythmia and an environment in which it is used.

FIG. 1 shows one embodiment of portions of a system for treating cardiac arrhythmia 100. System 100 includes an implantable pulse generator (PG) 105 that is coupled by a first cardiac lead 110 and a second cardiac lead 115, or one or more additional leads, to a heart 120 of a patient 125. Implantable PG 105 can take the form of a pacemaker, a defibrillator, or a defibrillator that includes pacing capability. System 100 also includes an external programmer 140 that provides for wireless communication with the implantable PG 105 using telemetry device 145. The first cardiac lead 110 and the second cardiac lead 115 each include a proximal end and a distal end, where the distal end of the leads 110 and 115 are implanted in, or on, the heart 120 at a first cardiac region and a second cardiac region, respectively. Each lead includes one or more electrodes that allow for combinations of either unipolar and/or bipolar sensing and delivery of energy to the heart 120 for pacing, and/or defibrillation. In some embodiments, the one or more electrodes include electrodes such as sensing, pacing, and shock electrodes.

Figure 2:
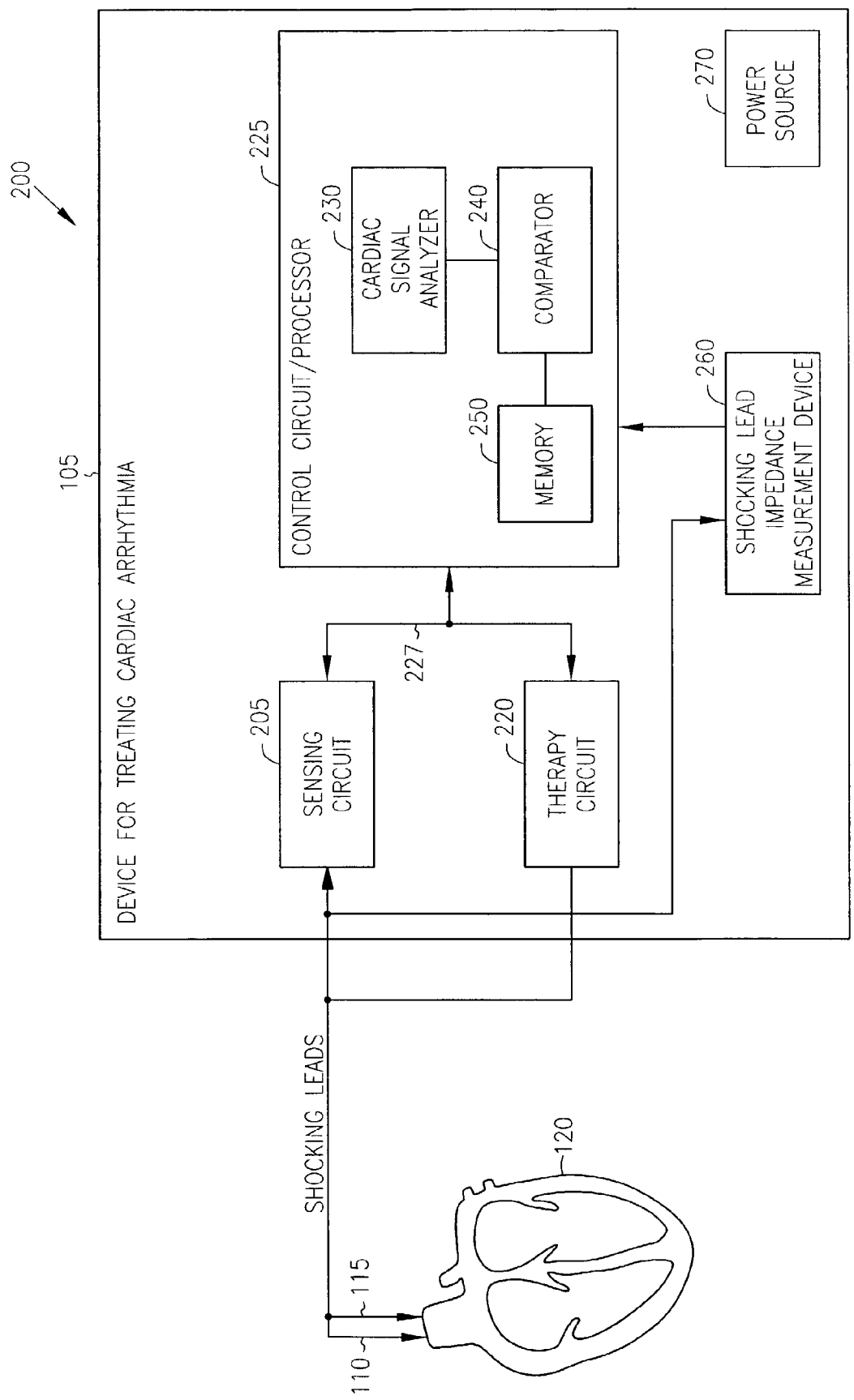
FIG. 2 is a block diagram of portions of a device for treating cardiac arrhythmia coupled to a heart.

FIG. 2 is a schematic diagram of one embodiment of portions of control circuitry 200 of an implantable PG 105 coupled to the heart 120. The implantable PG 105, as shown in FIG. 2, includes a sensing circuit 205 and a therapy circuit 220 coupled to shock leads 110 and 115. The implantable PG 105 further includes a shock lead impedance measurement device 260, a power source 270, and a control circuit/processor 225. In the embodiment shown, the control circuit/processor 225 incorporates a cardiac signal analyzer 230, a comparator 240, and a memory 250 to control implantable PG 105. In one embodiment, the functions of the analyzer 230 and the comparator 240 are implemented in software within the control circuit/processor 225.

Sensing circuit 205 is coupled to implantable leads 110 and 115. In some embodiments, sensing circuit 205 is coupled to multiple leads. Each of the leads includes one or more shock/pacing electrodes to deliver low/high energy therapy to the heart 120. The electrodes are disposed in multiple selected cardiac regions of the heart 120, such as the coronary sinus region, the ventricular region, and the superior vena cava region. The electrodes coupled to leads 110 and 115 can include sensing, pacing, and/or shock electrodes. Sensing circuit 205 receives cardiac signals from the sensing electrodes and amplifies the received cardiac signals.

Shock lead impedance measurement device 260 is coupled to the electrodes and measures shock lead electrode impedances by measuring impedance between each possible pair of electrodes that includes at least one shock electrode from all of the disposed electrodes. One example of a method for measuring defibrillation or shock lead impedance is to measure the voltage difference between the lead electrode and another electrode resulting from a test current sent through the lead to the other electrode. The impedance is then determined by dividing the measured voltage by the test current. This method is discussed in Linder et al. U.S. Pat. No. 6,317,628, entitled "Cardiac Rhythm Management System with Painless Lead Impedance Measurement System" and is incorporated by reference herein in its entirety, including its discussion of a lead impedance measurement of a defibrillation lead. Another example of a method for measuring defibrillation lead impedance is to calculate the impedance value from the voltage droop of a capacitively coupled output voltage pulse over a fixed period of time. This method is discussed in Citak U.S. Registered Invention No. H1,929, entitled "Cardiac Rhythm Management System with Lead Impedance Measurement" and is incorporated by reference herein in its entirety.

Each possible pair of electrodes can include two or more shock electrodes, a shock electrode and a pacing electrode, a shock electrode and a sensing electrode, a shock electrode and two or more pacing/sensing electrodes, and a shock electrode and a conductive housing that covers part of the implantable PG 105.

Comparator 240 which is coupled to the shock lead impedance measurement device 260, then compares each of the measured shock lead electrode impedances to a predetermined acceptable shock lead electrode impedance value. In some embodiments, the predetermined acceptable lead electrode impedance value is about 20 ohms.

If the lead electrode impedance measurement is greater than a predetermined value, analyzer circuit 230 which is coupled to comparator 240 allows shock therapy to be delivered through the lead. If the lead electrode impedance is less than or equal to the predetermined value, the lead is presumed to be in an electrically shorted condition and analyzer circuit 230 prevents delivery of shock therapy using that lead.

An electrically shorted shock electrode condition can occur when one or more dislodged shock electrodes can come in contact with one or more disposed sensing/pacing electrodes, a dislodged shock electrode coming in contact with one or more other disposed shock electrodes, and a shock electrode having exposed coils.

In some embodiments, analyzer circuit 230 sets a shorted lead indication corresponding to a shock electrode based on the outcome of the lead impedance measurement. In some embodiments, analyzer circuit 230 sets one or more shorted lead indications to each of the shock electrodes whose measured shock lead electrode impedances are below the predetermined acceptable shock lead acceptance value. In some embodiments, setting shorted lead indications comprises setting shorted lead flags. Setting shorted lead indications can also include writing to one or more locations in a memory 250. In some embodiments the shorted lead indications are cleared if the measured impedance value of the corresponding lead is greater than the predetermined value.

In one example embodiment, a first shock lead is coupled to at least one shock electrode which is adapted to be disposed around a coronary sinus regions of a heart 120. A second shock lead is coupled to multiple sensing/pacing/shock electrodes adapted to be disposed around the right atrium of the heart 120. A third shock lead is coupled to at least one pacing/shock electrode adapted to be disposed around the superior vena cava region of the heart 120. Therapy circuit 220 is coupled to the first electrode to deliver a high energy shock therapy to the coronary sinus region. Further, the therapy circuit 220 is coupled to the second and third electrodes to deliver low/high energy therapy to the right atrium and superior vena cava regions of the heart 120, respectively.

Therapy circuit 220 delivers high energy therapy to the coronary sinus region using the first lead if the lead electrode impedance is greater than the predetermined value. If the disposed shock lead in the coronary sinus region becomes dislodged and comes in contact with at least one of the other disposed electrodes in the right atrium or superior vena cava regions, the measured lead electrode impedance will be less than or equal to a predetermined value and delivery of shock therapy will be prevented. Delivery is prevented to maintain integrity of the therapy circuit 220 and to further ensure patient safety. Also in this embodiment, therapy circuit 220 delivers low/high energy therapy to the right atrial and superior vena cava regions based on the outcome of the impedance measurements. It can also be envisioned that the shock leads can be disposed in the ventricular region of the heart 120.

Figure 3:
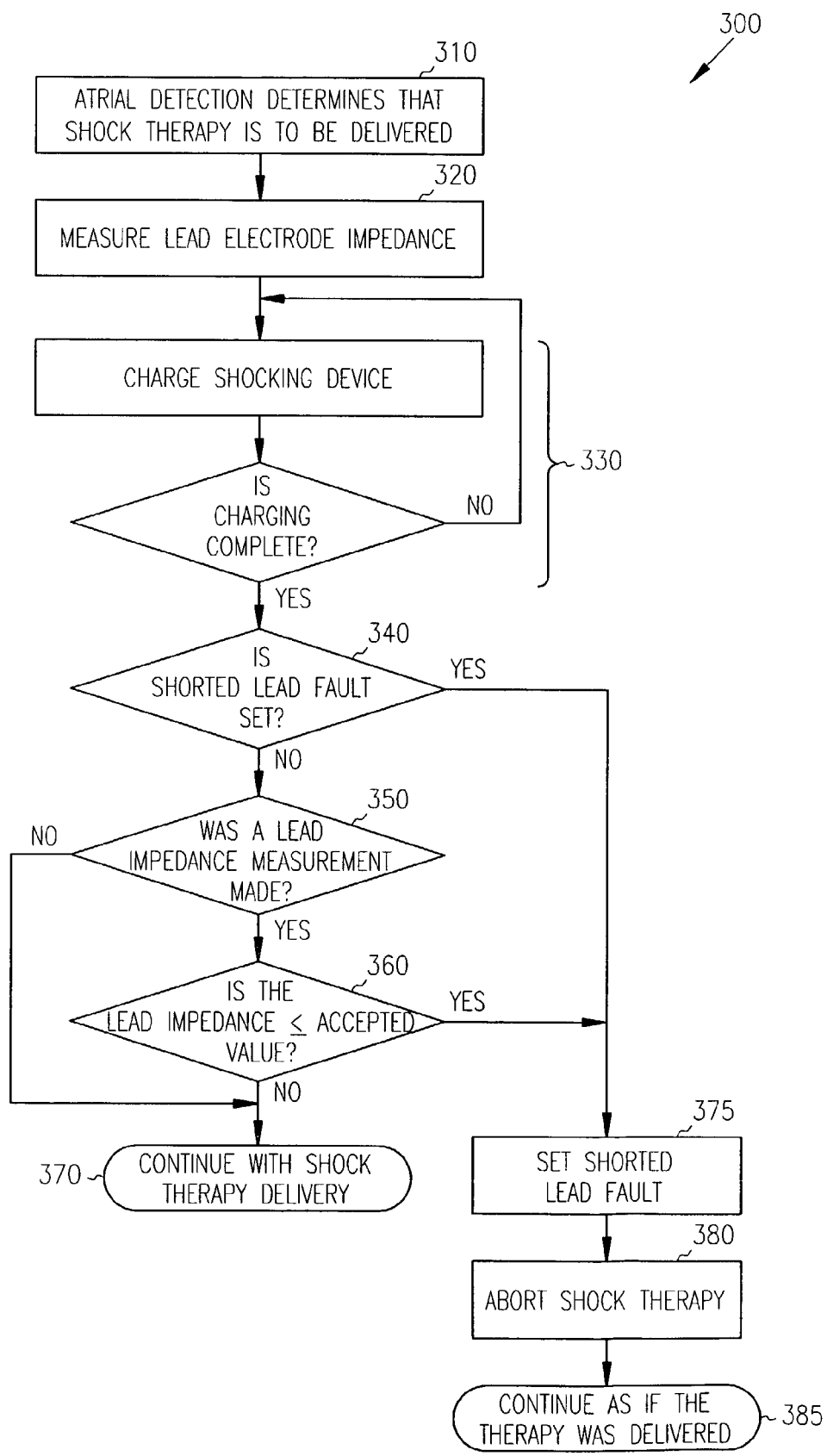
FIG. 3 is a flowchart showing one embodiment of a method of delivering shock therapy based on the result of a lead impedance measurement.

FIG. 3 is a flowchart illustrating one embodiment of a method 300 of delivering shock therapy based on the result of a lead electrode impedance measurement. At step 310, sensing leads disposed in the atrium detect that shock therapy is to be delivered. At step 320, shock lead electrode impedance is measured between each of all possible pairs of electrodes that include the shock electrode that is to be used to deliver the shock therapy. In some embodiments, shock leads includes electrodes such as pacing and sensing electrodes. In some embodiments, electrodes are disposed around multiple selected cardiac regions that include the coronary sinus region, ventricular region, the superior vena cava region, and the conductive housing covering a part of the implantable PG 105.

At step 330, therapy circuit 220 is charged. When the charging is completed, if a shorted lead fault 340 is not indicated and a lead electrode impedance measurement was made 350, at step 360 each of the measured shock lead electrode impedances is compared to a predetermined shock lead electrode impedance value. If the lead electrode impedance is greater than the predetermined value, at step 370 the shock therapy continues. In one embodiment, the predetermined shock lead electrode impedance value is approximately 20 ohms.

If the charging 330 is completed, a shorted lead fault 340 is not indicated, and a lead electrode impedance measurement was not made 350 or not completed, at step 370 the shock therapy continues.

If the charging 330 is completed, and either a shorted lead fault 340 is indicated, or a lead electrode impedance measurement was made 350 and the measured lead electrode impedance is less than or equal to a predetermined shock lead electrode impedance value 360, then a shorted lead fault is set to a fault state at step 375, the delivery of shock therapy is aborted at step 380, but the arrhythmia therapy is continued as if the shock therapy was delivered 385. In some embodiments the event of an aborted shock therapy delivery is logged as having occurred. After a predetermined number of logged events, no further deliveries of shock therapy are allowed. In one embodiment, the number of logged events is 6.

In some embodiments, shorted lead flags are cleared when the shorted leads are corrected. Generally, flags are cleared by a physician or a trained health care professional.

Figure 4:
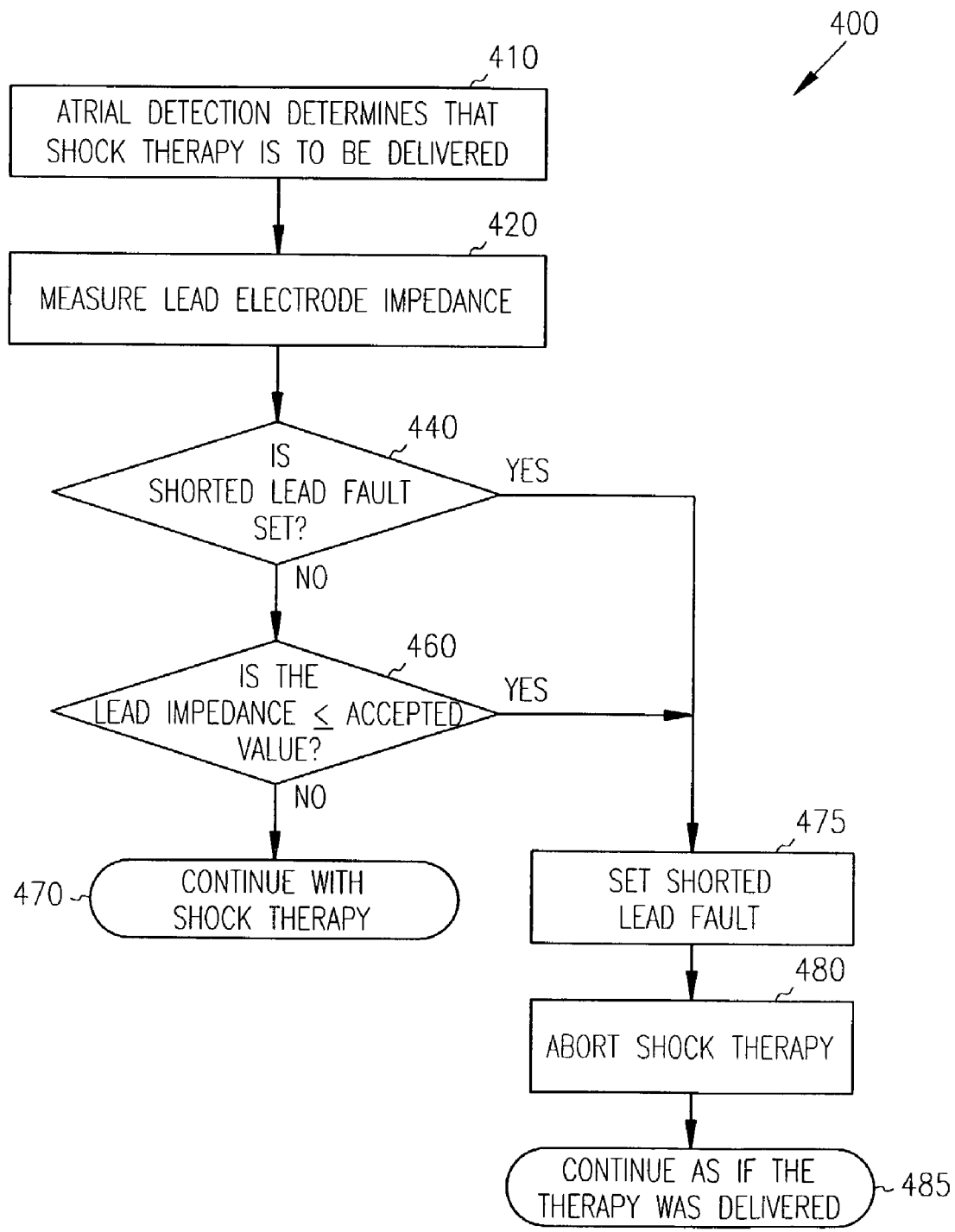
FIG. 4 is a flowchart showing another embodiment of a method of delivering shock therapy based on the result of a lead impedance measurement.

FIG. 4 is an alternate embodiment of the method shown in FIG. 3. In this embodiment the lead impedance is measured at step 420 and the shorted lead fault is checked at step 440 without charging the therapy circuit 220.

Figure 5:
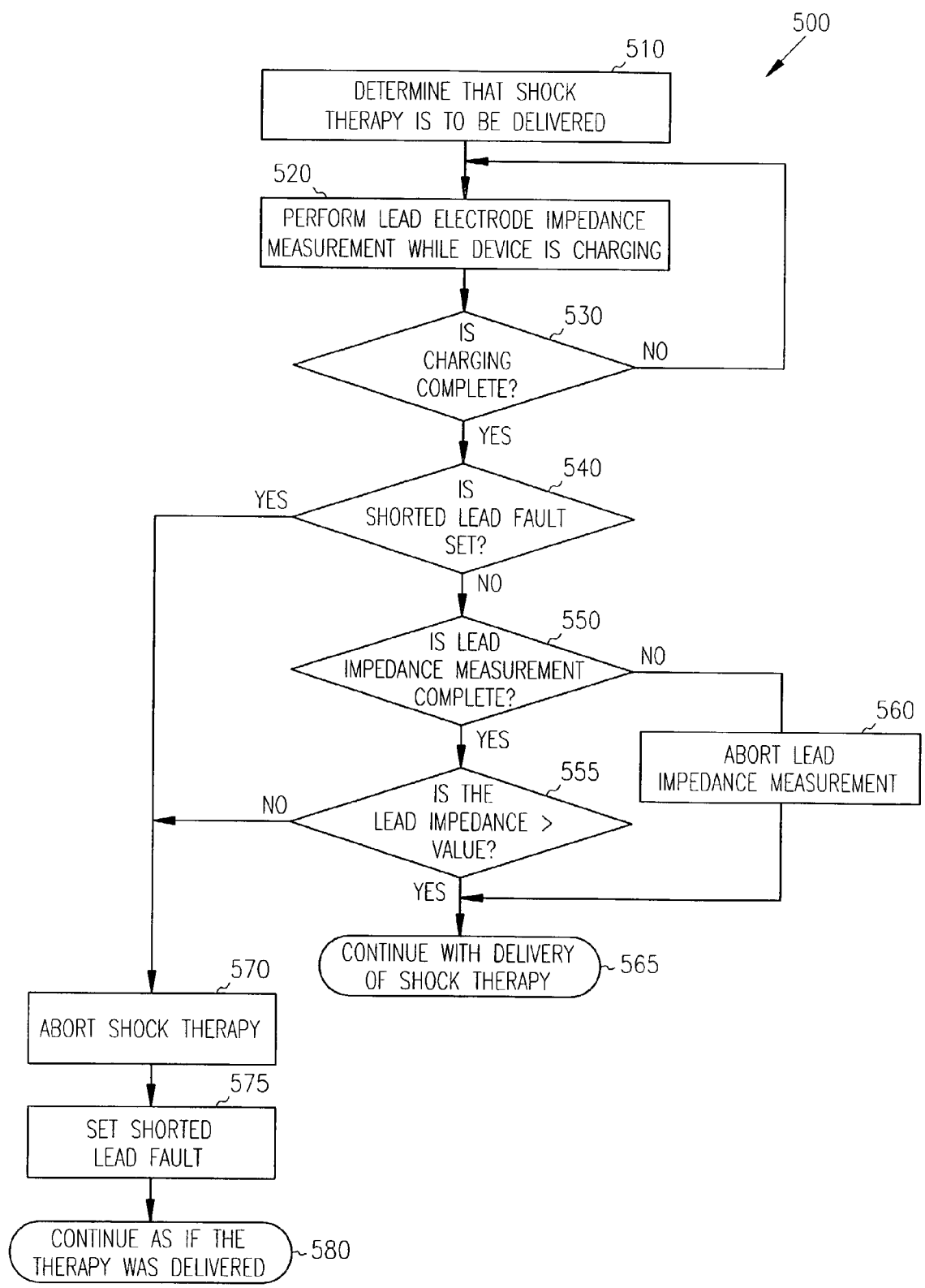
FIG. 5 is a flowchart showing another embodiment of a method of delivering shock therapy based on the result of a lead impedance measurement.

FIG. 5 is a flowchart illustrating another embodiment of a method 500 of delivering shock therapy based on the result of a lead electrode impedance measurement. At step 510, it is determined that shock therapy is to be delivered. At step 520, shock lead electrode impedance is measured between each of all possible pairs of electrodes that include the shock electrode that is going to be used to deliver the shock therapy while the therapy circuit 220 is charging. If charging is complete 530, a shorted lead fault is not indicated 540, the lead electrode impedance measurement was completed 550, and the lead electrode impedance value is greater than a predetermined impedance value 555, at step 565 the shock therapy continues. In one embodiment, the predetermined shock lead electrode impedance value is approximately 20 ohms.

If charging is complete 530, a shorted lead fault is not indicated 540, and the lead electrode impedance measurement is not complete 550, then at step 560 the lead electrode impedance measurement is aborted and at step 565 the delivery of shock therapy is continued.

If charging is complete 530, and either a shorted lead fault is indicated 540 or the lead electrode impedance measurement completed and the lead electrode impedance was not greater than the predetermined value, then the delivery of shock therapy is aborted at step 570, the shorted lead fault is set to a fault state at step 575, but the arrhythmia therapy is continued as if the shock therapy was delivered 580. In some embodiments continuing as if the shock therapy was delivered includes logging the event of an aborted shock therapy delivery as having occurred. After a predetermined number of logged events, no further deliveries of shock therapy are allowed.

Although specific examples have been illustrated and described herein, it will be appreciated by those of ordinary skill in the art that any other embodiment that exists that is calculated to achieve the same purpose may be substituted for the specific example shown. This application is intended to cover any adaptations or variations of the present invention. Therefore, it is intended that this invention be limited only by the claims and their equivalents.

What is claimed is:

1. An implantable apparatus for treating cardiac arrhythmia, the apparatus comprising:
    a plurality of implantable leads including at least one high-energy shock lead, wherein the leads include at least one electrode, and wherein at least one lead and lead electrode is adapted and arranged to deliver high and low energy therapy to at least one region of the heart;
    an impedance measurement circuit coupled to the plurality of electrodes adaptable to measure the impedance between electrodes in a plurality of pairs of electrodes;
    a control circuit coupled to the impedance measurement circuit, wherein the controller circuit is adapted to initiate a impedance measurement between a pair of electrodes outside a high-energy electrical stimulus, wherein the control circuit sets a shorted lead indicator to a fault state when the impedance between a pair of electrodes is less than a predetermined value, and wherein the control circuit is adapted to prevent the same high-energy shock stimulus when the shorted lead indicator is set to a fault state.

2. The apparatus of claim 1, wherein the impedance measurement circuit measures impedances between electrodes in a plurality of pairs of electrodes, each pair in the plurality having at least one shock electrode.

3. The apparatus of claim 1, wherein the control circuit sets one or more shorted lead indicators associated with each of the shock electrodes to a fault state when the measured impedance between pairs of electrodes is less than or equal to a predetermined value.

4. The apparatus of claim 3, wherein the processor coupled to the impedance measurement device clears the fault state of one more shorted lead indicators associated with each of the shock electrodes when the measured impedance between pairs of electrodes is greater than a predetermined value.

5. The apparatus of claim 4, wherein the predetermined value is about 20 ohms.

6. The apparatus of claim 1, wherein at least one implantable lead and lead electrode is adapted and arranged to sense cardiac signals occurring in at least one region of the heart including the Coronary Sinus region, the Superior Vena Cava region, and the Right Ventricular region.

7. A method of delivering shock therapy, the method comprising:
    determining that a condition exists for which shock therapy is to be delivered;
    measuring the impedance between electrodes in a plurality of pairs of electrodes, each pair in the plurality having at least one shock electrode;
    delivering the shock therapy using an electrode pair if the impedance between the electrode pair is greater than a predetermined value; and aborting the delivery of the shock therapy if the impedance between the electrode pair is less than or equal to a predetermined value.

8. The method of claim 7, wherein a shorted lead indicator is set to a fault condition if the electrode impedance is less than or equal to a predetermined value.

9. The method of claim 7, wherein the predetermined value is about 20 ohms.

10. The method of claim 7, wherein the electrode pair includes at least one electrode adapted and arranged for use in at least one region of heart including the regions of the Coronary Sinus, the Superior Vena Cava, or the Right Ventricle.

11. The method of claim 7, wherein aborting the delivery of shock therapy includes:
    continuing in an arrhythmia therapy algorithm as if the delivery of shock therapy had occurred;
    logging the event as a delivered therapy; and
    preventing the delivery of shock therapy after a predetermined number of delivered therapy events are logged.

12. A method of delivering shock therapy, the method comprising:
    determining that a condition exists for which shock therapy is to be delivered;
    measuring the impedance of a shock lead electrode while a shock therapy device is charging;
    delivering the shock therapy if the shock therapy device completed charging, the electrode impedance measurement was completed, and the measured electrode impedance is greater than a predetermined value;
    aborting the electrode impedance measurement if the shock therapy device completed charging but the electrode impedance measurement has not completed;
    continuing with the delivery of the shock therapy if the shock therapy device completed charging and the electrode impedance measurement has been aborted; and
    aborting the delivery of the shock therapy if the shock therapy device completed charging, the lead impedance measurement completed, and the electrode impedance is less than or equal to a predetermined value.

13. The method of claim 12, wherein the method includes setting a shorted lead indicator to a fault state if the electrode impedance is less than or equal to a predetermined value.

14. The method of claim 13, wherein the method includes:
    delivering the shock therapy if the shorted lead indicator is not set to a fault state;
    continuing with the delivery of shock therapy if the shock therapy device completed charging, if the electrode impedance measurement has been aborted, and if the shorted lead indicator is not set to a fault state; and
    aborting the delivery of the shock therapy if the shorted lead indicator is set to a fault state.

15. The method of claim 13 wherein the predetermined impedance value is about 20 ohms.

16. The method of claim 12 wherein measuring the impedance of a shock electrode includes measuring the impedance between electrodes in a plurality of pairs of electrodes, each pair in the plurality having at least one shock electrode.

17. The method of claim 16, wherein the electrode pair includes electrodes adapted for use in the Coronary Sinus region, the Superior Vena Region, and the Right Ventricular regions of the heart.

18. The method of claim 12, wherein aborting the delivery of shock therapy includes:
    continuing in an arrhythmia therapy algorithm as if the delivery of shock therapy had occurred;
    logging the event as a delivered therapy; and
    preventing the delivery of shock therapy after a predetermined number of delivered therapy events are logged.

* * * * *